United States Patent [19]

Williams et al.

[11] Patent Number: 4,526,888
[45] Date of Patent: Jul. 2, 1985

[54] NEPHROTOXICITY INHIBITORS FOR AMINOGLYCOSIDE ANTIBIOTICS

[75] Inventors: Patricia D. Williams, Peterboro; Girard H. Hottendorf, Manlius, both of N.Y.

[73] Assignee: Bristol-Myers Company, New York, N.Y.

[21] Appl. No.: 489,999

[22] Filed: Apr. 29, 1983

[51] Int. Cl.³ .................... A61K 37/00; A61K 31/70; C07G 7/00; C07C 103/52
[52] U.S. Cl. .......................................... 514/12; 514/2; 514/42; 514/25; 260/112.5 R; 260/112 R; 424/78
[58] Field of Search ............... 424/10, 177, 88, 85, 424/91, 180, 78, 79, 19, 20, 21, 22, 32, 47; 260/112.5, 112 R

[56] References Cited

U.S. PATENT DOCUMENTS 3,927,204 12/1975 Neri et al. .......................... 424/78
4,356,166 10/1982 Peterson et al. ..................... 424/19
4,409,247 10/1983 Baret et al. .......................... 426/41

OTHER PUBLICATIONS

Josepovitz et al., *J. Pharm. and Exp. Ther.* vol. 223, pp. 314–321, (1982).
Lipsky, J. J. *J. Pharm. and Exp. Ther.* vol. 215, pp. 390–393, (1980).
Kornguth et al. *J. Antimicrobial Chemotherapy* vol. 6, pp. 121–131, 1980.
Friedmann et al., *Chemical Abstracts*, vol. 94, No. 140387x, 1981 "Polymers with Potential Pharmacological Properties".

*Primary Examiner*—Thomas G. Wiseman
*Assistant Examiner*—Robin Teskin
*Attorney, Agent, or Firm*—Richard R. Lloyd

[57] ABSTRACT

This invention relates to the conjoint use of asparagine or aspartic acid polymers, e.g. poly-l-asparagine or poly-l-aspartic acid polymers, or copolymers thereof, with aminoglycoside antibiotics to inhibit the nephrotoxicity associated with aminoglycoside antibiotics.

23 Claims, 2 Drawing Figures

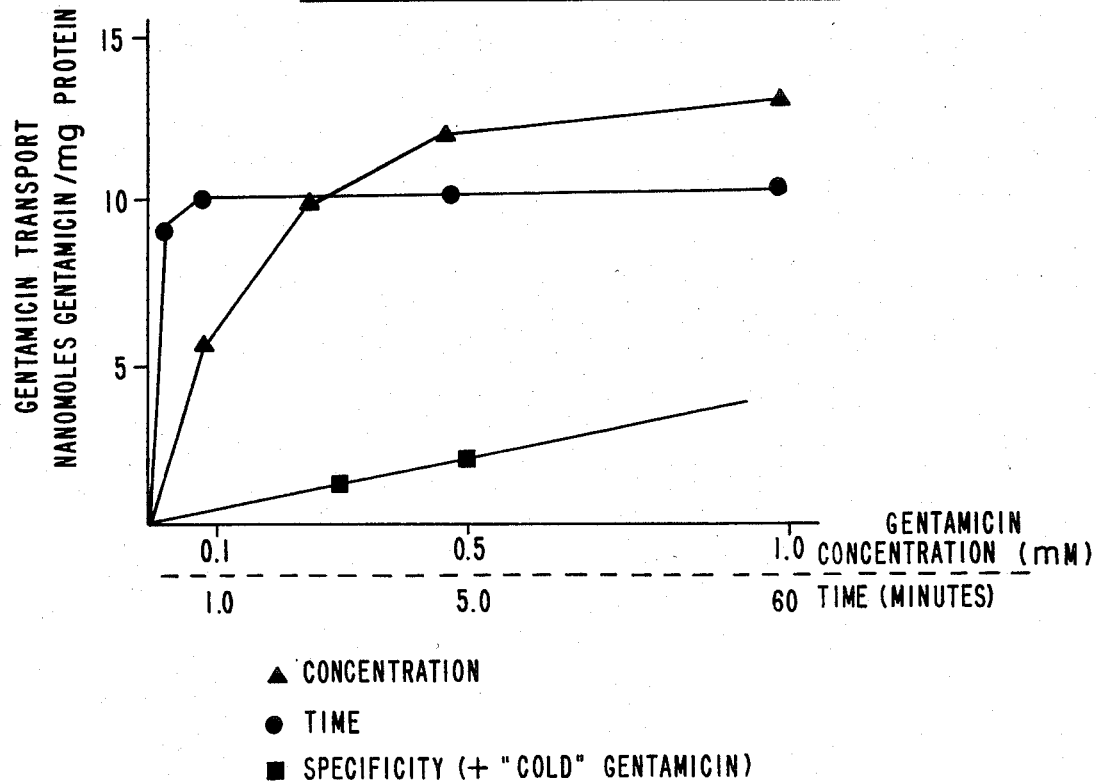
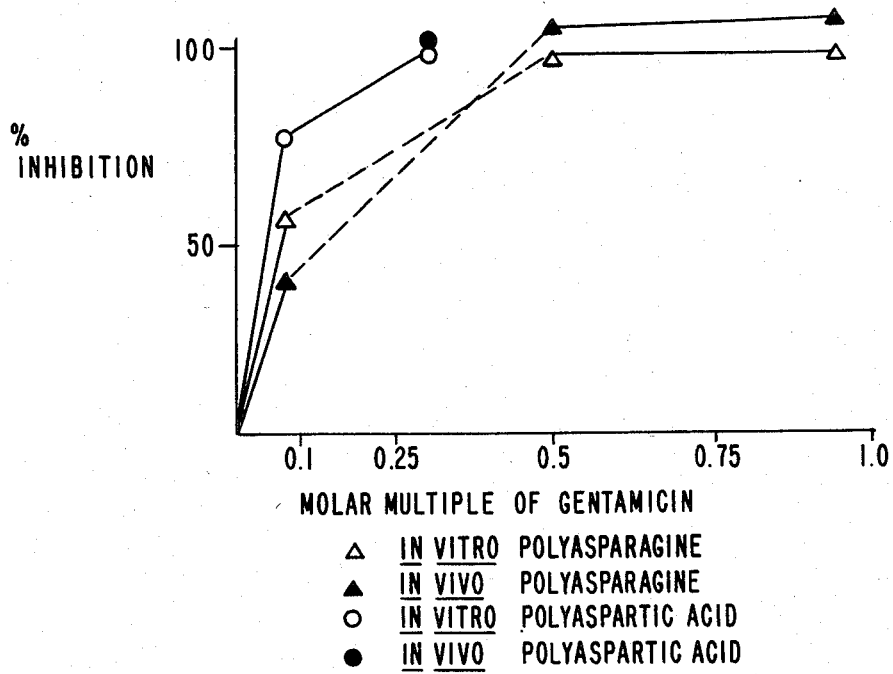

NEPHROTOXICITY INHIBITORS FOR AMINOGLYCOSIDE ANTIBIOTICS

SUMMARY OF THE INVENTION

The nephrotoxicity of aminoglycoside antibiotics is substantially reduced or eliminated by the conjoint use therewith of a polymer of asparagine (e.g. poly-l-asparagine) or aspartic acid (e.g. poly-l-aspartic acid), a copolymer thereof, or a copolymer of asparagine or aspartic acid with a comonomer.

BACKGROUND OF THE INVENTION

Aminoglycoside antibiotics, for example, gentamicin, are bound to and transported into the proximal tubule cells in the kidneys [Humes et al., *Am. J. Kidney Diseases* 11: 5–29 (1982)]. Proximal tubule cell necrosis and subsequent compromise of renal function results [Cronin, *Clinical Nephrology* 11: 251–256 (1979)]. This nephrotoxicity limits the clinical use of these lifesaving antibiotics [Cronin, *Clinical Nephrology* 11: 251–256 (1979); Bennett, *Mineral Electrolyte Metab.* 6: 277–86 (1981); Schor et al., *Kidney International* 19: 288–296 (1981)]. At present there is no safe means to limit or prevent aminoglycoside nephrotoxicity [Francke et al., *Infections in Surgery* March:205–214 (1983)].

A number of polyamines, some themselves potentially nephrotoxic, have been shown to inhibit binding and transport of aminoglycoside antibiotics in kidney tissue [Josephovitz et al., *J. Pharmacol. Exp. Ther.*, 223: 314–321 (1982)] or kidney subcellular fractions [spermine—Lipsky et al., *J. Pharmacol. Exp. Ther.*, 215: 390–393 (1980); and polyamines such as spermine, spermidine, polymyxin B and polylysine—Kornguth et al., *J. Antimicrob. Chemother.*, 6: 121–131 (1980)]. However, Josephovitz et al., supra, have questioned the use of organopolycations to reduce the nephrotoxic potential of aminoglycosides because of the possible nephrotoxicity associated with polycations as a class.

Methods for studying the transport of drugs and endogenous substances across epithelial cells such as those in the kidney include the use of isolated membrane vesicles; Murer et al., *J. Membrane Biol.*, 55: 81–95 (1980). Procedures for isolating and purifying brush border membranes from kidney tissue for the use described herein (in vitro membrane transport inhibition screening) have been reported; Williams et al., *Toxicology and Applied Pharmacology*, 61: 243–251 (1981) and Kinsella et al., *Biochimica et Biophysica Acta*, 552: 468–477 (1979). Gentamicin transport/binding studies using isolated renal membrane vesicles have been reported; Lipsky et al., supra, Sastraskih et al., *J. Pharmacol. Exp. Ther.*, 222: 350–358 (1982); kidney mitochondrial and microsomal binding inhibition have also been employed; Kornguth et al., supra. Josephovitz et al., supra, have conducted in vivo studies of inhibition of gentamicin uptake in rat renal cortex by organic polycations.

Applicants have found that certain neutral and anionic polyamino acids prevent or retard the membrane transport (in vitro) and nephrotoxicity (in vivo) of aminoglycoside antibiotics. Previously, only polycations have been reported to inhibit renal membrane binding or tissue accumulation of aminoglycosides. Reports of aminoglycoside nephrotoxicity inhibitors have been confined to unrelated substances such as fosfomycin [Inouye et al., *J. Pharm. Dyn.*, 5: 659–669 (1982)], glucarolactones/glycarolactams [Furunto et al., *Japan J. Pharmacol.*, 27: 371–378 (1977); *J. Antibiotics*, 29: 950–953 (1976); Furunto et al., *J. Antibiotics*, 29: 187–194 (1976); U.S. Pat. No. 4,122,171; U.S. Pat. No. 3,929,583, U.S. Pat. No. 3,962,429] and sodium formaldehyde bisulfite [Pindell et al., *Chemotherapia.*, 8: 163–174 (1964); British Pat. No. 957,433; German OS Nos. 2,641,388].

Description of the Invention

It has now been discovered that polymers of the neutral amino acid, asparagine, e.g. poly-l-asparagine and polymers of the acidic amino acid, aspartic acid, e.g. poly-l-aspartic acid, when conjointly administered to a mammal with a nephrotoxic aminoglycoside antibiotic, reduce the nephrotoxicity of the aminoglycoside antibiotic, apparently by inhibiting the renal uptake or binding of the aminoglycoside.

The aminoglycoside antibiotic which can be employed in conjunction with the renal uptake inhibiting polymers of the invention is any aminoglycoside antibiotic which accumulates in renal tissue, and thus comprises any aminoglycoside antibiotic. Examples of such aminoglycoside antibiotics include kanamycin (Merck Index 9th ed. #5132), gentamicin (Merck Index 9th ed. #4224), amikacin (Merck Index 9th ed. #A1), dibekacin (Merck Index 9th ed. #2969), tobramycin (Merck Index 9th ed. #9193), neomycin (Merck Index 9th ed. #6278), streptomycin (Merck Index 9th ed. #8611/8612), paromomycin (Merck Index 9th ed. #6844), sisomicin (Merck Index 9th ed. #8292), and netilmicin, all known in the art. The useful antibiotics include the several structural variants of the above compounds (e.g. kanamycin A, B and C; gentamicin A, $C_1$, $C_{1a}$, $C_2$ and D; neomycin B and C and the like).

All aminoglycoside antibiotics tested to date accumulate in renal tissue and possess a certain nephrotoxic potential [Luft et al., *J. Inf. Dis.*, 138(4): 541–595 (1978)]. Thus, the present invention is useful with any aminoglycoside antibiotic. The free bases, as well as pharmaceutically acceptable acid addition salts of these aminoglycoside antibiotics, can be employed.

For the purpose of this disclosure, the terms "pharmaceutically acceptable acid addition salt" shall mean a mono or poly salt formed by the interaction of one molecule of the aminoglycoside antibiotic with one or more moles of a pharmaceutically acceptable acid. Included among those acids are acetic, hydrochloric, sulfuric, maleic, phosphoric, nitric, hydrobromic, ascorbic, malic and citric acid, and those other acids commonly used to make salts of amine-containing pharmaceuticals.

The renal uptake inhibitors conjointly used with the nephrotoxic aminoglycosides of this invention are polymers of asparagine or aspartic acid, including homopolymers of each, copolymers with each other and pharmaceutically acceptable copolymers of asparagine and/or aspartic acid with comonomers, which copolymers contain a major amount of asparagine or aspartic acid. The useful polymers have a molecular weight between about 1000 and about 100,000, preferably between about 5500 and about 16,000, and most preferably between about 8000 and 15,000. Where the polymer is poly-l-aspartic acid or contains aspartic acid as a copolymer, it may be employed as a pharmaceutically acceptable salt, for example, as the sodium salt.

The combinations of the invention can be conjointly used in a variety of modes. Preferably, the aminoglycoside antibiotic and the inhibitory polymer are combined into a single dosage unit, preferably with a pharmaceutically acceptable carrier, for example, a cosolution or dispersion in an inert pharmaceutically acceptable solvent or dispersing agent or the like. Typically, pharmaceutically acceptable carriers can be any of those heretofore employed or compatible with the aminoglycoside antibiotic, alone.

Alternatively, but less preferably, the inhibitory polymer can be separately formulated with pharmaceutically acceptable materials and administered separately, preferably substantially concurrently, with the aminoglycoside antibiotic or, less preferably, within about an hour before or after administration of the aminoglycoside antibiotic.

The mode of administration, the dosage and frequency of dosage is governed by the mode of administration and dosage considerations conventionally employed with the aminoglycoside antibiotic. Thus, for example, various of the combinations of the invention can be administered intramuscularly or intravenously, or otherwise, as dictated by medical and pharmacological practice related to the desired use of the particular antibiotic employed.

The proportional and absolute amounts of the antibiotic and the inhibitory polymer are subject to variation. Typically, the antibiotic is employed in its conventional art recognized therapeutic amounts. In the tests described in the Examples, below, the inhibitory polymer did not reduce the antimicrobial activity of the aminoglycoside antibiotic.

The amount of inhibitory polymer employed in conjunction with the aminoglycoside antibiotic is an aminoglycoside antibiotic nephrotoxicity reducing amount. The amount varies depending upon the aminoglycoside employed. Typically, the amount of inhibitory polymer employed is at least about 0.002 moles and preferably at least about 0.005 moles of the polymer per mole of the aminoglycoside antibiotic. The upper limit is dictated by practical weight and cost considerations. Amounts as high as 10 moles of polymer per mole of antibiotic have been considered, but appear to be unnecessary as much lower levels appear to provide excellent inhibition.

BRIEF DESCRIPTION OF THE DRAWINGS

FIG. 1 is a graphic representation of gentamicin transport characterized as to time and concentration dependency, and as to specificity.

FIG. 2 is a graphic comparison of potencies of transport inhibition of in vivo nephrotoxicity inhibition of poly-l-asparagine and poly-l-aspartic acid.

The following examples should be considered illustrative rather than limiting. All parts and percentages throughout the specification are by weight unless otherwise specified. It is noted that in the following examples commercial gentamicin is employed, which is a mixture of gentamicins $C_1$ (~28%), $C_2$ (~37%) and $C_{1a}$ (~35%). Thus, the weighted average molecular weight is about 462.6. Also, the poly-l-asparagines employed in the examples are polymers consisting of approximately 80-90 repeating units, with molecular weights of approximately 9000-10,000 (provided by supplier). The poly-l-aspartic acids employed in the examples are the sodium salts of polymers consisting of approximately 90-100 repeating units, with a molecular weight near 14,000 (provided by supplier).

EXAMPLE 1

An in vitro screening program was established to study the selective inhibition of aminoglycoside transport across renal brush border membranes of proximal tubule cells. The screening tests employed isolated, purified brush border membrane as described by Kinsella et al., *Biochem. Biophys. Acta.*, 552: 468-477 (1979) and Williams et al., *Tox. Applied Pharmacol.*, 61: 243-251 (1981), comprising isolation and purification of rat renal cortical membranes via differential centrifugation, cationic precipitation and discontinuous sucrose gradient techniques. The transport assay was conducted by incubation of $^3$H-gentamicin sulfate with brush border membrane vesicles followed by collection of the vesicles onto Millipore filters under vacuum. The transport was quantified by liquid scintillation techniques as described by Kinsella et al., *J. Pharmacol. Exp. Ther.*, 209: 443-450 (1979). Gentamicin transport was characterized, FIG. 1, as to time and concentration dependency, and as to specificity. Gentamicin transport was then measured at a fixed concentration of gentamicin (0.5 mM) in the presence of prospective inhibitors at 5X molar concentration.

Specifically, the membrane transport assay comprised incubating 0.4 millimolar $^3$H-gentamicin or $^3$H-amikacin with 100-200 micrograms of membrane in a 100 microliter reaction volume for 30 seconds (the reaction initiated by the addition of the membrane protein—approximately 20 microliters). Following the 30 second reaction the transport was quenched by addition of 2.0 ml of ice cold buffer (250 millimolar mannitol, 15 millimolar KCl and 20 millimolar Hepes-pH 7.4 with TRIS). The reaction media was then vacuum filtered on 0.3 micron Millipore filters. The filters were washed twice with 2 ml of the buffer and removed and counted using liquid scintillation spectroscopy techniques.

Transport inhibition was measured by monitoring the above transport assays in the presence of the prospective inhibitors at initial concentrations ranging from 1-10 times the aminoglycoside molar concentration. The inhibitors were solubilized in the above-described buffer.

Table I lists various chemicals screened in this in vitro test.

TABLE I

| Chemicals Screened In Vitro | |
|---|---|
| SUGARS/DERIVATIVES (16) | POLYAMINES (14) |
| Acetylgalactosamine | Agmatine |
| Acetylglucosamine | Diaminodecane |
| Acetylmannosamine | Diaminodipropylamine |
| Galactosamine | Diaminododecane |
| Glucarolactam | Diaminoheptane |
| Glucarolactone | Diaminooctane |
| Gluconolactone | Diethylenetriamine- |
| Glucuronamide | pentaacetic acid |
| Glucuronic acid | Dimethylaminopropyl- |
| Glucuronolactone | amine |
| Glucose | Hexanediamine |
| Lyxosylamine | Spermine |
| Mannose | Tributylamine |
| Methylglucamine | Triethylenediamine |
| 3-0-Methylglucose | Triethylenetetramine |
| Xylose | Tripropylamine |
| MISCELLANEOUS (19) | AMINO ACIDS |
| Amikacin tetragluconate | MONO (8)    POLY (12) |
| Caffeine | alanine    alanine$_{42}$ |
| Calcium chloride | asparagine    asparagine$_{90}$ |
| Cationized ferritin | arginine    arginine$_{390}$ |
| Cytidine | cystathione    ornithine$_{90}$ |
| Fosfomycin | cysteine    histidine$_{70}$ |

TABLE I-continued

| Chemicals Screened In Vitro | | |
|---|---|---|
| Glutaraldehyde | glutamine | $glutamine_2$ |
| Glutaric acid | glycine | $glutamic\ acid_{60}$ |
| Lysozyme | lysine | $lysine_{2,4,10,20}$ |
| Myoinositol phosphate | | $aspartic\ acid_{90}$ |
| Polyadenylic acid | | |
| Polycytidylic acid | | |
| Renal dipeptidase inhibitor (BCH-1) | | |
| Sialic acid | | |
| Sodium acetone bisulfite | | |
| Sodium aldehyde bisulfite | | |
| Sodium bisulfite | | |
| Sodium formaldehyde bisulfite | | |
| Sodium glutaraldehyde bisulfite | | |
| TERTIARY AMINES (4) | | |
| Choline | | |
| Tetrabutylammonium bromide | | |
| Tetraethylammonium bromide | | |
| Tetrahexylammonium bromide | | |

Table II presents the fourteen (14) chemicals which were found to inhibit gentamicin transport using this screening procedure. These transport inhibitors differ markedly in potency as is reflected by molar multiples producing 50% transport inhibition.

TABLE II

| Membrane Transport Inhibitors | |
|---|---|
| Inhibitors | $I_{50}$ |
| Polyamines | |
| Diaminodipropylamine | 10X |
| Spermine | 3X |
| Polyamino Acids | |
| $Lysine_4$ | 10X |
| $Lysine_{10}$ | 1X |
| $Lysine_{20}$ | 0.05X |
| $Asparagine_{90}$ | 0.1X |
| $Aspartic\ acid_{90}$ | <0.1X |
| $Glutamic\ acid_{60}$ | <0.1X |
| $Ornithine_{90}$ | <2X |
| $Histidine_{70}$ | 1X |
| $Arginine_{390}$ | 0.05X |
| Miscellaneous | |
| Sodium formaldehyde bisulfite | 10X |
| Sodium glutaraldehyde bisulfite | 10X |
| Cationized ferritin | $10^{-9}$ |

Nephroprotective agents were examined for compatibility with amikacin or gentamicin by *Bacillus subtilis* cup plate assay. No evidence of loss in aminoglycoside activity was observed in any of the combinations. The membrane transport inhibitors were also assayed alone to ascertain any antibiotic activity which might influence the interpretation of data on the combinations. None of the inhibitors showed any detectable antimicrobial activity versus *B. subtilis*.

In vivo data on nine (9) transport inhibitors from the in vitro screening is presented in Table III.

TABLE III

| Membrane Transport Inhibitors In Vivo | | | |
|---|---|---|---|
| | Multiple of AG Dose | | Nephroprotective |
| Inhibitor | Molar | Mg | Activity |
| $Lysine_4$ | 16 | 25 | 0 |
| $Lysine_{10}$ | 0.3 | 15 | 0 |
| $Lysine_{20}$ | 0.1 | 0.7 | + |
| NaFormBisulfite | 136 | 40 | + |
| NaGlutBisulfite | 5 | 2.5 | 0 |
| Diaminodipropylamine | 5 | 1 | 0 |
| $Aspartic\ acid_{90}$ | 0.3 | 10 | +++ |
| $Glutamic\ acid_{60}$ | 1 | 15 | 0 |
| $Asparagine_{90}$ | 1.0 | 20 | +++ |

TABLE III-continued

| Membrane Transport Inhibitors In Vivo | | | |
|---|---|---|---|
| | Multiple of AG Dose | | Nephroprotective |
| Inhibitor | Molar | Mg | Activity |
| " | 0.5 | 10 | +++ |
| " | 0.3 | 6 | + |
| " | 0.15 | 3 | + |
| " | 0.10 | 2 | + |

+ = less than 50% reduction
+++ = reduction 100%

For compounds such as polyasparagine and polyaspartic acid which showed the greatest degree of in vivo nephroprotective activity, an excellent correlation exists between molar in vitro and in vivo potency. This relationship is demonstrated in FIG. 2. In the polylysine series of membrane transport inhibitors, in vitro potency showed a correlation with polymer size, and only the most potent transport inhibitor ($polylysine_{20}$) showed any nephroprotective activity (see Table III).

EXAMPLE II

A number of candidates from the above in vitro screening were subjected to in vivo studies.

In Vivo Animal Model

A fourteen (14) day subacute nephrotoxicity model in rats was utilized to test the in vivo efficacy of aminoglycoside-transport inhibitor combinations. This model parallels short course treatment regimens in the clinic. Though blood urea nitrogen (BUN) was monitored as a clinical parameter of renal function, the primary evaluation of nephrotoxicity in this model involves histopathologic examination of renal tissue, which is a more accurate and sensitive method for assessing nephrotoxicity [Hottendorf et al., *Antimicrob. Agents Chemother.*, 18: 176–181 (1980)]. The dose of gentamicin necessary to elicit a significant and reproducible nephrotoxic response in this model is 20 mg/kg/day (bid, 14 days).

TEST ANIMALS

Male Sprague-Dawley rats [Charles River Breeding Laboratories, Inc., (CRL: COBS CD (SD) BR)] approximately 6 weeks old and weighing 140–160 gms upon arrival were used. They were conditioned for at least 5 days prior to the start of the study. Only animals found to be clinically healthy were selected. Rats were identified individually by number on the tail with black marking pens. During the study the rats were housed individually in cages of the appropriate size and type in a temperature-controlled room. Rodent Laboratory Chow (pellet, Purina Ralston Company) and water was offered ad libitum.

TEST ARTICLES AND CONTROL PROCEDURES

Garamycin (gentamicin sulfate) containing 40 mg gentamicin base/ml.
Poly-l-$asparagine_{90}$ ($PAsp_{90}$), (Sigma Chemical Co., St. Louis, Mo.).
Poly-l-aspartic $Acid_{90}$ ($PAA_{90}$), (Sigma Chemical Co., St. Louis, Mo.).
Poly-l-glutamic $Acid_{60}$ ($PGlu_{60}$), (Sigma Chemical Co., St. Louis, Mo.).
Tetralysine ($PLys_4$), pentahydrochloride salt, (University of Sherbrooke, Sherbrooke, Quebec, Canada).

Gentamicin base concentrations were determined in all dosing solutions once during the study. Activity was determined by *Bacillus subtilis* cup plate assay.

DOSE PREPARATION AND PROCEDURES

The aminoglycoside and aminoglycoside-inhibitor mixtures were administered subcutaneously twice daily for 14 days.

Gentamicin dosing solutions were prepared by diluting the commercial Garamycin (40 mg/ml) to a concentration of 4 mg/ml (1:10 dilution). This solution was diluted with equal volumes of water or the appropriate solutions of the other test agents to a final concentration of 2 mg gentamicin base/ml. The grouping of rats and descriptions of dosing solutions and volumes are presented in Tables IV and V below.

TABLE IV

| Group No. | Animal Number | Treatment | Molar Ratio | Doses (mg/kg*) |
|---|---|---|---|---|
| I | 51–60 | Saline | — | — |
| II | 26–30 | Gentamicin | — | 10 |
| III | 31–35 | Gentamicin | — | 20 |
| IV | 1–5 | Gentm/PAsp$_{90}$ | 7:1 | 20:60 |
| V | 6–10 | Gentm/PAsp$_{90}$ | 3.5:1 | 20:120 |
| VI | 11–15 | Gentm/PAA$_{90}$ | 3:1 | 20:200 |
| VII | 16–20 | Gentm/PGlu$_{60}$ | 1:1 | 20:350 |
| VIII | 21–25 | Gentm/PLys$_{4}$ | 1:16 | 20:500 |

Due to the cloudiness and decreased activity of Group IV dosing solution Gentm/PAsp$_{90}$ molar ratio 7:1 (20:60 mg/kg) study animals #1–5 were discontinued dosing on study Day 2 and saline control animals #56–60 were dosed with a different concentration of that combination and were substituted and reassigned study animals #1–5, Group IV.

TABLE V

| Group No. | Treatment | Initial conc. (mg/ml) Aminogly. | Initial conc. (mg/ml) Other | Final Conc. (mg/ml) Aminogly. | Final Conc. (mg/ml) Other | Daily Half Dose (mls/100 gm) |
|---|---|---|---|---|---|---|
| I | Saline | — | — | — | — | 1.00 |
| II | Gentm | 4.00 | — | 2.00 | — | 0.25 |
| III | Gentm | 4.00 | — | 2.00 | — | 0.50 |
| IV | Gentm/PAsp$_{90}$ | 20.0 | 60.0 | 10.0 | 30.0 | 0.10 |
| V | Gentm/PAsp$_{90}$ | 4.00 | 24.00 | 2.00 | 12.00 | 0.50 |
| VI | Gentm/PAA$_{90}$ | 4.00 | 40.00 | 2.00 | 20.00 | 0.50 |
| VII | Gentm/PGlu$_{60}$ | 4.00 | 70.00 | 2.00 | 35.00 | 0.50 |
| VIII | Gentm/PLys$_{4}$ | 4.00 | 100.00 | 2.00 | 50.00 | 0.50 |

ANATOMICAL PATHOLOGY

All rats were euthanized by an overdose of sodium pentobarbital on study Day 15.

The kidneys were removed and examined grossly. A longitudinal section of the left kidney and a cross section of the right kidney from each rat were preserved in 10% neutral buffered Formalin for histopathological evaluation. Tissue sections (6 μm each) were stained with hematoxylin and eosin, and the resulting tissue slides were randomized, masked, and examined by a single pathologist without knowledge of the animal's treatment.

Lesions encountered in the renal cortex included tubular vacuolar or granular degeneration, peritubular inflammation, tubular necrosis, tubular dilatation, tubular basophilia, and interstitial fibrosis. The extent and distribution of each of these lesions in both kidneys of every rat were scored as follows: 0, absence of lesion; 1, lesion represented in fewer than 10% of the nephrons; 2, lesion represented in 10 to 50% of the nephrons; 3, lesion represented in 50 to 90% of the nephrons; and 4, lesion represented in more than 90% of the nephrons. Since these lesions are all interrelated and represent various stages of proximal tubular damage, the lesion scores were summed to produce a single nephrotoxicity response for each animal, with a possible severity range of 0 to 24.

The results of the histopathology evaluation is summarized as follows.

TABLE VI

| Animal Number | Histopath. Score (TOTAL) | Animal Number | Histopath. Score (TOTAL) |
|---|---|---|---|
| Group I SALINE CONTROLS | | Group II GENTM 10 | |
| 51 | 2 | 26 | 1 |
| 52 | 0 | 27 | 5 |
| 53 | 3 | 28 | 6 |
| 54 | 2 | 29 | 4 |
| 55 | 3 | 30 | 5 |
| | 2.0 | | 4.2 |
| Group III GENTM 20 | | Group IV GENTM/PAsp (20:60) | |
| 31 | 4 | 1 | 2 |
| 32 | 3 | 2 | 2 |
| 33 | 5 | 3 | 3 |
| 34 | 4 | 4 | 3 |
| 35 | 8 | 5 | 4 |
| | 4.8 | | 2.8 |
| Group V GENTM/PAsp (20:120) | | Group VI GENTM/PAA (20:200) | |
| 6 | 3 | 11 | 2 |
| 7 | 4 | 12 | 0 |
| 8 | 3 | 13 | 3 |
| 9 | 3 | 14 | 3 |
| 10 | 2 | 15 | 1 |
| | 3.0 | | 1.8 |
| Group VII GENTM/PGlu (20:350) | | Group VIII GENTM/Plys$_4$ (20:500) | |
| 16 | 6 | 21 | 4 |
| 17 | 8 | 22 | 7 |
| 18 | 5 | 23 | 5 |
| 19 | 10 | 24 | 5 |
| 20 | 8 | 25 | 8 |
| | 7.4 | | 5.8 |

Groups II and III demonstrate the nephrotoxicity of gentamicin. Groups IV, V and VI demonstrate the inhibitory effect of the invention. Groups VII and VIII demonstrate the comparative lack of inhibitory effect of other potential inhibitors outside the scope of the invention.

EXAMPLE III

In order to determine the potential of several in vitro inhibitors of gentamicin transport to prevent aminoglycoside nephrotoxicity in rats, poly-l-lysine (Plys$_{10,12}$), Poly-l-asparagine$_{90}$ (PAsp$_{90}$) and sodium formaldehyde bisulfite (MeS) were coadministered with amikacin and gentamicin as mixtures for fourteen days subcutaneously. Nephrotoxicity was monitored by blood urea nitrogen (BUN) analysis and histopathologic examination of renal tissue.

TEST ARTICLES AND CONTROL PROCEDURES (a) Amikin (amikacin sulfate) containing 250 mg amikacin base per ml.
(b) Garamycin (gentamicin sulfate) containing 40 mg gentamicin base per ml.
(c) Poly-l-lysine$_{10}$ (Plys$_{10}$), Sigma Chemical Co., St. Louis, Mo.
(d) Poly-l-lysine$_{12}$ (Plys$_{12}$), Miles Laboratories, Inc., Elkhart, Ind.
(e) Poly-l-asparagine$_{90}$ (PAsp$_{90}$), Sigma Chemical Co., St. Louis, Mo.
(f) Sodium Formaldehyde Bisulfite (MeS), Eastman Kodak Co., Rochester, N.Y.
(g) Amikacin and gentamicin base concentrations were determined in all dosing solutions once during the study. Agents prepared in mixtures with amikacin or gentamicin were also analyzed for bioactivity separately in concentrations used in mixtures. Activity was determined by *Bacillus subtilis* cup plate assay.

TEST ANIMALS

Male Sprague-Dawley rats [Charles River Breeding Laboratories, Inc., [CRL: COBS CD (SD) BR)] approximately six weeks old and weighing 130–150 gms upon arrival were used. They were conditioned for at least five days prior to the start of the study. Only animals found to be clinically healthy were selected. Rats were identified individually by number on the tail with black marking pens.

During the study rats were housed individually in cages of the appropriate type and size in a temperature-controlled room. Rodent Laboratory Chow (pellet, Purina Ralston Company) and water were offered ad libitum.

DOSE PREPARATION AND PROCEDURES

Aminoglycosides and aminoglycoside-inhibitor mixtures were administered subcutaneously twice daily for fourteen days.

Amikacin solutions were prepared by first diluting the commercial Amikin (250 mg/ml) with Sterile Water for Injection, USP, to a concentration of 20 mg/ml (1:12.5 dilution). Gentamicin solutions were prepared similarly by diluting the commercial Garamycin (40 mg/ml) to a concentration of 4 mg/ml (1:10 dilution). These solutions were diluted with equal volumes of water or the appropriate solutions of the other test agents to a final concentration of 10 mg amikacin or 2 mg gentamicin base/ml. The grouping of rats and descriptions of dosing solutions and volumes are presented in the tables below.

TABLE VII

| Group No. | Animal Number | Treatment | Molar Ratio | Doses (mg/kg*) |
|---|---|---|---|---|
| I | 46–55 | Saline | — | — |
| II | 36–40 | Gentamicin | — | 20 |
| III | 11–15 | Gentm/PAsp$_{90}$ | 1:1 | 20:400 |
| IV | 1–5 | Gentm/Plys$_{12}$ | 1:1 | 20:125 |
| V | 6–10 | Gentm/Plys$_{10}$ | 1:3 | 20:275 |
| VI | 16–20 | Gentm/MeS | 1:68 | 20:400 |
| VII | 21–25 | Gentm/MeS | 1:136 | 20:800 |
| VIII | 26–30 | Amik/MeS | 1:9 | 200:400 |
| IX | 31–35 | Amik/MeS | 1:18 | 200:800 |
| X | 41–45 | Amikacin | — | 200 |

*in terms of base activity

TABLE VIII

| Group No. | Treatment | Initial Conc. (mg/ml) Aminogly. | Initial Conc. (mg/ml) Other | Final Conc. (mg/ml) Aminogly. | Final Conc. (mg/ml) Other | Daily Half Dose (mls/100 gm) |
|---|---|---|---|---|---|---|
| I | Saline | — | — | — | — | 1.0 |
| II | Gentamicin | 4.00 | — | 2.00 | — | 0.5 |
| III | Gentm/PAsp$_{90}$ | 4.00 | 80.00 | 2.00 | 40.00 | 0.5 |
| IV | Gentm/Plys$_{12}$ | 4.00 | 25.00 | 2.00 | 12.50 | 0.5 |
| V | Gentm/Plys$_{10}$ | 4.00 | 55.00 | 2.00 | 27.50 | 0.5 |
| VI | Gentm/MeS | 4.00 | 80.00 | 2.00 | 40.00 | 0.5 |
| VII | Gentm/MeS | 4.00 | 160.00 | 2.00 | 80.00 | 0.5 |
| VIII | Amik/Mes | 20.00 | 40.00 | 10.00 | 20.00 | 1.0 |
| IX | Amik/Mes | 20.00 | 80.00 | 10.00 | 40.00 | 1.0 |
| X | Amikacin | 20.00 | — | 10.00 | — | 1.0 |

CLINICAL AND ANATOMICAL PATHOLOGY

Blood was collected from all rats on study Day 15 for determination of blood urea nitrogen (BUN).

All rats were euthanized by an overdose of sodium pentobarbital on study Day 15. The kidneys were removed, examined grossly and placed in 10% neutral buffered formalin for subsequent histopathologic evaluation.

TABLE IX

Histopathological Study Results

| Rat Number | Histopath. Score (TOTAL) | Rat Number | Histopath. Score (TOTAL) |
|---|---|---|---|
| Group I SALINE CONTROLS | | Group II GENTAMICIN (20 mg/kg) | |
| 46 | 2 | 36 | 8 |
| 47 | 2 | 37 | 9 |
| 48 | 2 | 38 | 9 |
| 49 | 0 | 39 | 8 |
| 50 | 0 | 40 | 10 |
| 51 | 3 | | 8.8 |
| 52 | 3 | | |
| 53 | 2 | | |
| 54 | 0 | | |
| 55 | 2 | | |
| | 1.6 | | |
| Group III GENT/PAsp$_{90}$* | | Group IV GENT/plys$_{12}$ (1:1) | |
| 11 | 1 | 1 | 11 |
| 12 | 5 | 2 | 6 |
| 13 | 2 | 3 | 5 |
| 14 | 2 | 4 | 5 |
| 15 | 1 | 5 | 4 |
| | 2.2 | | 6.2 |
| Group V GENT/Plys$_{10}$ (1:3) | | Group VI GENT/MeS (1:68) | |
| 6 | 4 | 16 | 5 |
| 7 | 8 | 17 | 7 |
| 8 | 4 | 18 | 4 |
| 9 | 8 | 19 | 8 |
| 10 | 11 | 20 | 5 |

TABLE IX-continued

| Histopathological Study Results | | | |
|---|---|---|---|
| Rat Number | Histopath. Score (TOTAL) | Rat Number | Histopath. Score (TOTAL) |
| | 7.0 | | 5.8 |
| Group VII GENT/MeS (1:136) | | Group VIII AMIK/MeS (1:9) | |
| 21 | 3 | 26 | 14 |
| 22 | 7 | 27 | 15 |
| 23 | 3 | 28 | 14 |
| 24 | 3 | 29 | 13 |
| 25 | 8 | 30 | 11 |
| | 4.8 | | 13.4 |
| Group IX AMIK/MeS (1:18) | | Group X AMIKACIN (200 mg/kg) | |
| 31 | 13 | 41 | 15 |
| 32 | 14 | 42 | 11 |
| 33 | 14 | 43 | 12 |
| 34 | 8 | 44 | 14 |
| 35 | 10 | 45 | 14 |
| | 11.8 | | 13.2 |

*At this dose, PAsp caused vaculolation in the proximal tubules which appears to be related to the presence of PAsp. The significance of this change is unknown.

Group II demonstrates the nephrotoxicity of gentamicin in this test. Group III demonstrates the inhibitory effect of the invention. Groups IV through IX demonstrate the comparative lack of inhibitory effect of other potential inhibitors outside the scope of the invention. Group X demonstrates the nephrotoxicity of amikacin in this test.

EXAMPLE IV

The potential of poly-l-asparagine and poly-l-aspartic acid to prevent amikacin nephrotoxicity in rats was determined by coadministering these agents with amikacin as mixtures for fourteen days subcutaneously. Nephrotoxicity was monitored by histopathologic examination of renal tissue.

TEST ARTICLES AND CONTROL PROCEDURES
(a) Amikin (amikacin sulfate) containing 250 mg amikacin base per ml.
(b) Poly-l-asparagine$_{80}$ (PAsp$_{80}$), molecular weight approximately 9000.
(c) Poly-l-aspartic acid$_{100}$ (PAA$_{100}$), molecular weight about 14,000.
(d) Amikacin base concentrations were determined on all dosing solutions once during the study. Activity was determined by *Bacillus subtilis* cup plate assay.

TEST ANIMALS
Twenty-five (25) male Sprague-Dawley rats [Charles River Breeding Laboratories, Inc., (CRL: COBS CD (SD) BR)] approximately 6 weeks old and weighing 130–150 gms upon arrival were used. They were conditioned for at least 5 days prior to the start of the study. Only animals found to be clinically healthy were selected. Rats were identified individually by number (1–25) on the tail with black marking pens.

During the study the rats were housed individually in cages of the appropriate size and type in a temperature-controlled room. Rodent Laboratory Chow (pellet, Purina Ralston Company) and water were offered ad libitum.

DOSE PREPARATION AND PROCEDURES
Amikacin and amikacin mixtures were administered subcutaneously twice daily for 14 days.

The amikacin dosing solutions were prepared by diluting the commercial Amikin (250 mg/ml) with Sterile Water for Injection, USP, to an initial concentration of 20 mg/ml (1:12.5 dilution). This solution was then diluted with equal volumes of sterile water or the appropriate solutions of the other test agents to a final concentration of 10 mg amikacin/ml.

TABLE X

| Group Identification | | | | |
|---|---|---|---|---|
| Group No. | Animal No. | Treatment | Molar Ratio | Doses (mg/kg*) |
| I | 1–5 | Amik/PAsp$_{80}$ | 5:1 | 200:600 |
| II | 6–10 | Amik/PAA$_{100}$ | 10:1 | 200:500 |
| III | 11–15 | Amikacin | — | 200 |
| IV | 16–25 | Saline | — | — |

*in terms of base activity

TABLE XI

| | | Dosing Solutions and Volumes | | | | |
|---|---|---|---|---|---|---|
| Group No. | Treatment | Initial Conc. (mg/ml) Amikacin | Other | Final conc. (mg/ml) Amikacin | Other | Daily Half Dose (mls/100 gm) |
| I | Amik/PAsp$_{80}$ | 20 | 60 | 10 | 30 | 1.00 |
| II | Amik/PAA$_{100}$ | 20 | 50 | 10 | 25 | 1.00 |
| III | Amikacin | 20 | — | 10 | — | 1.00 |
| IV | Saline | — | — | — | — | 1.00 |

ANATOMICAL PATHOLOGY
All rats were euthanized by an overdose of sodium pentobarbital on study Day 15. The kidneys were removed, examined grossly and placed in 10% neutral buffered formalin for subsequent histopathologic evaluation.

TABLE XII

| Histopathological Study Results | | | |
|---|---|---|---|
| Rat Number | Histopath. Score (TOTAL) | Rat Number | Histopath. Score (TOTAL) |
| Group I Amikacin/PAsp$_{80}$ (5:1) | | Group II Amikacin/PAA$_{100}$ (10:1) | |
| 1 | 2 | 6 | 0 |
| 2 | 3 | 7 | 6 |
| 3 | 5 | 8 | 3 |
| 4 | 5 | 9 | 3 |
| 5 | 1 | 10 | 4 |
| | 3.2 | | 3.2 |
| Group III Amikacin | | Group IV Saline | |
| 11 | 12 | 16 | 3 |
| 12 | 13 | 17 | 3 |
| 13 | 11 | 18 | 3 |
| 14 | 13 | 19 | 2 |
| 15 | 15 | 20 | 1 |
| | 12.8 | 21 | 3 |
| | | 22 | 0 |
| | | 23 | 2 |
| | | 24 | 1 |
| | | 25 | 1 |
| | | | 1.9 |

We claim:

1. An aminoglycoside composition having reduced nephrotoxicity, which comprises:
   (a) an aminoglycoside, or pharmaceutically acceptable salt thereof, and
   (b) at least 0.002 moles, per mole of aminoglycoside, of a member selected from the group consisting of
      (i) polyasparagine,
      (ii) polyaspartic acid or a pharmaceutically acceptable salt thereof,
      (iii) a copolymer of polyasparagine and polyaspartic acid, or a pharmaceutically acceptable salt thereof, and
      (iv) a copolymer of polyasparagine or polyaspartic acid, or a pharmaceutically acceptable salt thereof, with a pharmaceutically acceptable co-monomer, said copolymer containing a substantial amount of asparagine or aspartic acid,
   wherein the member has a molecular weight of from about 1000 to about 100,000.

2. The composition of claim 1 which comprises:
   (a) an aminoglycoside, or pharmaceutically acceptable salt thereof, and
   (b) at least 0.005 moles, per mole of aminoglycoside, of poly-l-asparagine or poly-l-aspartic acid, or a pharmaceutically acceptable salt thereof,
   wherein the polymer has a molecular weight of from about 5500 to about 16,000.

3. The composition of claim 2 wherein the aminoglycoside is gentamicin or amikacin.

4. The composition of claim 1 which comprises gentamicin, or a pharmaceutically acceptable salt thereof, and at least about 0.005 moles, per mole of gentamicin, of poly-l-asparagine having a molecular weight of from about 8000 to about 15,000.

5. The composition of claim 1 which comprises gentamicin, or a pharmaceutically acceptable salt thereof, and at least about 0.005 moles, per mole of gentamicin, of poly-l-aspartic acid having a molecular weight of from about 8000 to about 15,000, or a pharmaceutically acceptable salt thereof.

6. The composition of claim 1 which comprises amikacin, or a pharmaceutically acceptable salt thereof, and at least about 0.005 moles, per mole of amikacin, of poly-l-asparagine having a molecular weight of from about 8000 to about 15,000.

7. The composition of claim 1 which comprises amikacin, or a pharmaceutically acceptable salt thereof, and at least about 0.005 moles, per mole of amikacin, of poly-l-aspartic acid having a molecular weight of from about 8000 to about 15,000, or a pharmaceutically acceptable salt thereof.

8. An aminoglycoside composition having reduced nephrotoxicity, in unit dosage form, which comprises:
   (a) a therapeutically effective amount of an aminoglycoside antibiotic and
   (b) a nephrotoxicity-reducing amount of a member selected from the group consisting of
      (i) polyasparagine,
      (ii) polyaspartic acid or a pharmaceutically acceptable salt thereof,
      (iii) a copolymer of polyasparagine and polyaspartic acid, or a pharmaceutically acceptable salt thereof, and
      (iv) a copolymer of polyasparagine or polyaspartic acid, or a pharmaceutically acceptable salt thereof, with a pharmaceutically acceptable co-monomer, said copolymer containing a substantial amount of asparagine or aspartic acid,
   wherein the polymer or copolymer has a molecular weight of from about 1000 to about 100,000.

9. The composition of claim 8 which additionally contains a pharmaceutically acceptable carrier.

10. The composition of claim 8 wherein the polymer or copolymer has a molecular weight of from about 8000 to about 15,000.

11. The composition of claim 10 which additionally contains a pharmaceutically acceptable carrier.

12. The composition of claim 10 wherein the polymer is poly-l-asparagine or poly-l-aspartic acid, or a pharmaceutically acceptable salt thereof, and is present in an amount of at least about 0.005 moles per mole of aminoglycoside antibiotic.

13. The composition of claim 12 which additionally contains a pharmaceutically acceptable carrier.

14. The composition of claim 12 wherein the aminoglycoside is gentamicin or amikacin.

15. The composition of claim 14 which additionally contains a pharmaceutically acceptable carrier.

16. A method of reducing the nephrotoxicity of an aminoglycoside antibiotic which comprises concurrently administering to a patient:
   (a) a therapeutically effective amount of an aminoglycoside antibiotic and
   (b) a nephrotoxicity-reducing amount of a member selected from the group consisting of
      (i) polyasparagine,
      (ii) polyaspartic acid or a pharmaceutically acceptable salt thereof,
      (iii) a copolymer of polyasparagine and polyaspartic acid, or a pharmaceutically acceptable salt thereof, and
      (iv) a copolymer of polyasparagine or polyaspartic acid, or a pharmaceutically acceptable salt thereof, with a pharmaceutically acceptable co-monomer, said copolymer containing a substantial amount of asparagine or aspartic acid,
   wherein the member has a molecular weight of from about 1000 to about 100,000.

17. The method of claim 16 wherein the aminoglycoside and the polymer or copolymer are administered in a pharmaceutically acceptable carrier.

18. The method of claim 16 wherein the polymer or copolymer has a molecular weight of from about 8000 to about 15,000.

19. The method of claim 18 wherein the aminoglycoside and the polymer or copolymer are administered in a pharmaceutically acceptable carrier.

20. The method of claim 18 wherein the polymer is poly-l-asparagine or poly-l-aspartic acid, or a pharmaceutically acceptable salt thereof, and is present in an amount of at least 0.005 moles per mole of aminoglycoside antibiotic.

21. The method of claim 20 wherein the aminoglycoside and polymer are administered in a pharmaceutically acceptable carrier.

22. The method of claim 20 wherein the aminoglycoside is gentamicin or amikacin.

23. The method of claim 22 wherein the aminoglycoside and polymer are administered in a pharmaceutically acceptable carrier.

* * * * *